United States Patent [19]
Iwama

[11] Patent Number: 5,241,962
[45] Date of Patent: Sep. 7, 1993

[54] CALCULUS DISINTEGRATING APPARATUS AND METHOD WITH AUTOMATIC THRESHOLD VALUE SETTING FUNCTION

[75] Inventor: Nobuyuki Iwama, Tochigi, Japan

[73] Assignee: Kabushiki Kaisha Toshiba, Kawasaki, Japan

[21] Appl. No.: 757,471

[22] Filed: Sep. 10, 1991

[30] Foreign Application Priority Data

Sep. 10, 1990 [JP] Japan .................. 2-237133

[51] Int. Cl.$^5$ ............................................. A61B 17/22
[52] U.S. Cl. ........................ 128/660.03; 128/24 EL
[58] Field of Search ........ 128/24 EL, 660.03, 24 AA; 73/584, 602, 627; 367/95, 98

[56] References Cited

U.S. PATENT DOCUMENTS

| | | | |
|---|---|---|---|
| 4,803,995 | 2/1989 | Ishida et al. | 128/24 EL |
| 4,986,259 | 1/1991 | Aida et al. | 128/24 EL |
| 4,991,604 | 2/1991 | Wurster et al. | 128/660.03 |
| 5,065,740 | 11/1991 | Itoh | 128/24 EL |
| 5,076,277 | 12/1991 | Iwama et al. | 128/24 EL |
| 5,092,336 | 3/1992 | Fink | 128/24 EL |

FOREIGN PATENT DOCUMENTS

| | | |
|---|---|---|
| 0337056 | 10/1989 | European Pat. Off. . |
| 0383629 | 8/1990 | European Pat. Off. . |
| 0460536 | 12/1991 | European Pat. Off. ....... 128/24 EL |
| 0461479 | 12/1991 | European Pat. Off. ....... 128/24 EL |
| 3621935 | 1/1988 | Fed. Rep. of Germany ... 128/24 EL |
| 2600521 | 12/1987 | France . |
| WO89/02724 | 4/1989 | World Int. Prop. O. . |

*Primary Examiner*—Lee S. Cohen
*Assistant Examiner*—Krista M. Pfaffle
*Attorney, Agent, or Firm*—Foley & Lardner

[57] ABSTRACT

To disintegrate a calculus present within a biological body under medical examination, the following steps are employed: irradiating ultrasonic pulses to an interior region of the biological body which contains at least the calculus; receiving echo pulses reflected from the interior region of the biological body to produce reflection signals; detecting both a maximum signal level and a minimum signal level from the reflection signals received during a predetermined time period; setting a first threshold value based on both of said maximum signal level and said minimum signal level; and, focusing a shock wave onto the calculus contained in the interior region of the biological body only while signal levels of the reflection signals exceed the first threshold value.

13 Claims, 5 Drawing Sheets

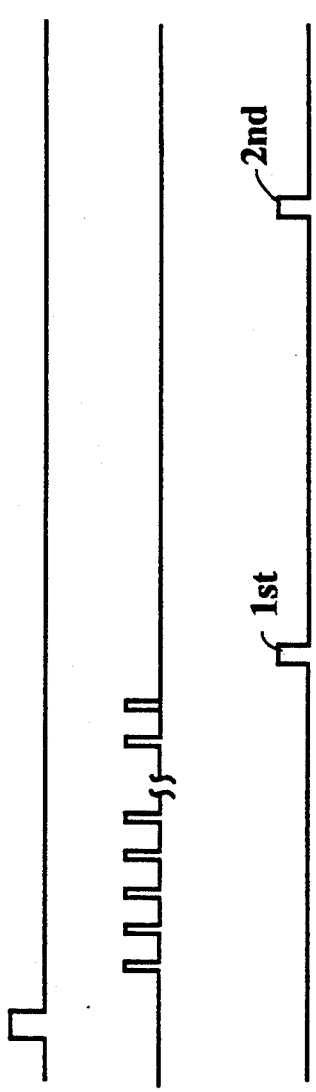
FIG.5A  START SWITCH 23
FIG.5B  ULTRASONIC PULSES FOR DETECTING MAX 40 / MIN 42
FIG.5C  SHOCK WAVES
FIG.5D  ECHO PULSES
(JUDGING ECHO PULSE 60)

CALCULUS DISINTEGRATING APPARATUS AND METHOD WITH AUTOMATIC THRESHOLD VALUE SETTING FUNCTION

BACKGROUND OF THE INVENTION

1. Field of the Invention

The present invention generally relates to a calculus disintegrating apparatus and a method thereof capable of focusing shock waves onto a calculus or concretion located within a biological body under medical examination so as to destroy or disintegrate the calculus. More specifically, the present invention is directed to a calculus disintegrating method and apparatus with an automatic threshold value setting function for shock waves.

2. Description of the Prior Art

Various calculus disintegrating or destroying apparatuses have been widely utilized in the medical field, in which shock waves generated outside a biological body under medical examination are focused onto calculi or concretions present in an organ (e.g., kidney) in order to disintegrate or destroy these calculi. It is well known, as a shock wave generating source, employments of an electrode discharge, an electromagnetic induction plate or an explosive compound (blasting powder). Very recently, a piezoelectric element has been employed as the shock wave generating source, since such a calculus disintegrating apparatus with employment of the piezoelectric elements owns a particular advantage, for instance, compactness, low cost and less consuming products.

In general, shock wave energy caused by shock waves focused onto a focal point has a sufficiently high value capable of disintegrating or destroying calculi or concretions. In addition, however, if the shock waves are mistakenly focused onto a soft tissue around the calculi, there are risks that hematoma and the like are formed in this soft tissue, i.e., harmful side effects. Under such circumstances, controlling methods to precisely project the shock waves only to the calculi, have been demanded.

Generally speaking, such controlling methods have been proposed: Prior to a shock-wave application, ultrasonic pulses having low energy (signal levels) are previously irradiated to the biological body and reflection waves (echoes) from an area near a focal point are detected. Thereafter, a judgement is made whether or not a focusing operation can be achieved by comparing the signal strengths of the echo signals with a predetermined value. That is, when the signal strength of the echo signals is greater than this value, it can be judged that the ultrasonic waves are focused onto the calculi, whereby shock waves can now be irradiated onto the calculi.

As is known, since an acoustic impedance of a calculus is higher than that of a soft tissue positioned near this calculus, a strength (level) of reflection (echo) signal from the calculus is higher than that from the soft tissue. Accordingly, it can be recognized that when a reflection signal having a high signal strength is received, the ultrasonic pulses are focused onto a calculus. Conversely, when a reflection signal having a low signal strength is received, since the ultrasonic pulses are not focused onto the calculus (namely, focused onto the soft tissue near the calculus), irradiation of shock waves is interrupted.

FIG. 1 shows one conventional calculus disintegrating apparatus utilizing the above-described characteristics of reflection signals, which is described in, for instance, U.S. Pat. No. 4,819,621 to Ueberle et al, entitled "METHOD FOR DETECTION OF CAVITATIONS DURING MEDICAL APPLICATION OF HIGH SONIC ENERGY".

In the conventional calculus disintegrating apparatus of FIG. 1, a piezoelectric element 1 having a shape of a spherical cup is employed. The piezoelectric element 1 functions as a shock wave generating source. At a center hole 1A of this piezoelectric element 1, an ultrasonic imaging probe 2 is mounted by which the shock waves may be focused onto a calculus 3. That is, the ultrasonic probe 2 performs an ultrasonic scanning operation with respect to a region covering this calculus 3 to acquire echo signals. The echo signals are processed so as to reconstruct an ultrasonic image of this scanned region in an ultrasonic diagnostic apparatus 10 and the reconstructed image is displayed on a TV monitor 11. As a result, an operator can control the shock waves to be focused onto the calculus 3, while observing this ultrasonic image displayed on the TV monitor 11.

There are two different types of power sources, i.e., a high-voltage power source 7 and a low-voltage power source 8. A pulser 4 is connected via a voltage selection switch 12 to these power sources 7 and 8. When the high-voltage power source 7 is connected via the switch 12 to the pulser 4, shock waves are generated from the piezoelectric element 1. Also, when the low-voltage power source 8 is connected via the switch 12 to the pulser 4, ultrasonic pulses with low levels which never produce such shock waves are generated from this piezoelectric element 1. Either the shock waves or the ultrasonic pulses generated from the piezoelectric element 1 are reflected from the calculus 3 and are returned as echoes to the piezoelectric element 1, so that these echoes are converted into electric signals which are then supplied to a receiver 5.

When the ultrasonic pulses are generated by energizing the piezoelectric element 1 under the low-voltage power source 8, the receiver 5 detects the echoes thereof to obtain the reflection signals. The reflection signals are then supplied to a judging circuit together with a preset threshold value derived from a threshold value setting circuit 13. The judging circuit 6 compares the above reflection signals with this threshold value. When the level of the reflection signal is higher than the threshold value, the judging circuit 6 makes a decision that the ultrasonic pulses generated from the piezoelectric element 1 are just focused onto the calculus 3. Accordingly, the judging circuit 6 controls the switch 12 in order that the pulser 4 is selectively connected from the low-voltage power source 8 to the high-voltage power source 7. As a result, the shock wave irradiation from the piezoelectric element 1 to the calculus 3 is now prepared. A display output circuit 9 is provided, whereby an image produced from the reflection signals obtained by the receiver 5 is displayed on the TV monitor 11.

In the above-described conventional calculus disintegrating apparatus, there are the following drawbacks. Since there are variations in sizes, shapes and positions of calculi, depending upon individual patients, even when the shock waves having the same or similar strengths are irradiated to the calculi or concretions, strengths (levels) of reflection signals obtained by the receiver 5 are different from each other. Under such circumstances, the threshold value is not always determined as a constant value. Therefore, the threshold value setting operations by way of the threshold value setting circuit 13 must be carried out every time the patients are diagnosed, which then gives heavy workloads to the operator.

To the contrary, if such a threshold value setting operation would not be performed for several patients, erroneous judgments could be made. That is, for instance, although the ultrasonic pulses are surely focused onto the calculus 3, the judging circuit 6 never instructs that the low-voltage power source 8 should be turned OFF and the high-voltage power source 7 should be turned ON so that no shock wave is generated from the piezoelectric element 1. In the worst case, since the shock waves would be irradiated to a normal tissue which need not be cured, this normal tissue could be destroyed, which would cause a serious medical problem.

SUMMARY OF THE INVENTION

The present invention has been made in an attempt to solve the above-described conventional problems, and therefore has an object to provide a calculus disintegrating apparatus and method with an automatic threshold value setting function.

To achieve the above-described object, a method for disintegrating a calculus (3) positioned within a biological body (30) under medical examination, comprising the steps of:

irradiating ultrasonic pulses to an interior region of the biological body (30) which contains at least the calculus (3) during a predetermined time period;

receiving echo pulses reflected from the interior region of the biological body (30) to produce reflection signals during said predetermined time period;

detecting both a maximum signal level (40) and a minimum signal level (42) from the reflection signals received during said predetermined time period;

setting a first threshold value ($T_h$) based on both of said maximum signal level (40) and said minimum signal level (42); and, focusing a shock wave onto the calculus (3) contained in the interior region of the biological body (30) only while signal levels of the reflection signals exceed the first threshold value ($T_h$).

Furthermore, a calculus disintegrating apparatus (100), according to the present invention, comprising:

means (1:4:8) for irradiating ultrasonic pulses to an interior region of a biological body (30) which contains at least a calculus (3) during a predetermined time period;

means (1:5) for receiving echo pulses reflected from the interior region of the biological body (30) to produce reflection signals during said predetermined time period;

means (20) for detecting both a maximum signal level (40) and a minimum signal level (42) from the reflection signals received during said predetermined time period;

means (21) for setting a first threshold value ($T_h$) based upon both of said maximum signal level (40) and said minimum signal level (42);

means (6) for judging whether or not signal levels of the reflection signals exceed the first threshold value ($T_h$) to produce a judging signal; and, means (1:4:7) for focusing a shock wave onto the calculus (3) contained in the interior region of the biological body (30) in response to the judging signal.

BRIEF DESCRIPTION OF THE DRAWINGS

For a better understandings of the present invention, reference is made of the following detailed description of the invention to be read in conjunction with the following drawings, in which.

DETAILED DESCRIPTION OF THE PREFERRED EMBODIMENTS

Basic Idea

A basic idea of the calculus disintegrating apparatus according to the present invention will now be summarized.

First, a shock wave generating source such as a piezoelectric element is energized by a low-voltage power source in order to generate ultrasonic waves, not shock waves. While irradiating the ultrasonic waves to an interior (containing calculi) of a biological body for a predetermined time period, signal strengths or levels of echo (reflection) signals are continuously monitored so as to detect a maximum value and a minimum value. A threshold value is determined based on both the maximum value and minimum value. For instance, this threshold value is determined within a range between the maximum value and minimum value, e.g., an averaged value among them.

Subsequently, ultrasonic waves are further irradiated and then signal strengths of echo signals are compared with this threshold value. If the compared signal strengths are higher than this threshold value, since these ultrasonic waves are surely focused onto calculi to be disintegrated, the shock wave generating source is energized by a high-voltage power source at this time. As a result, desirable shock waves are produced and focused onto the calculi for disintegration purpose. After this application of the shock waves, the above-described threshold value setting operation is automatically repeated.

Accordingly, the proper threshold values can be automatically, continuously set before application of the shock waves to the biological body, taking account of the maximum/minimum values of the reflection signals. In other words, the automatically set threshold values correctly reflect variations in individual bodies. Therefore, an operator can surely control the shock waves to be just focused on the calculus to be disintegrated.

Overall Arrangement of First Calculus Disintegrating Apparatus

Figure 2:
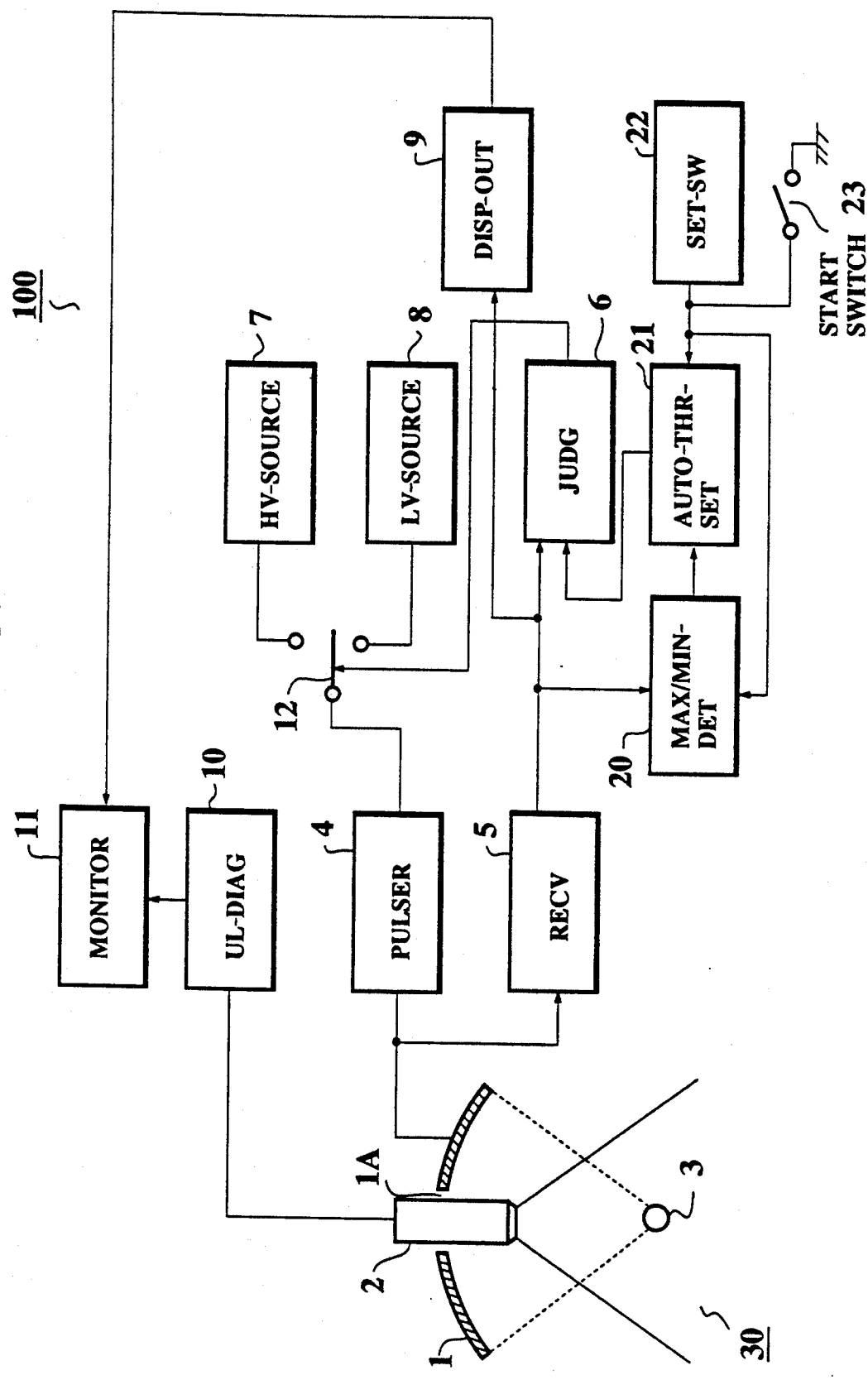
FIG. 2 is a schematic block diagram of a calculus disintegrating apparatus 100 according to a first preferred embodiment of the present invention.

Referring now to FIG. 2, an overall arrangement of a calculus disintegrating apparatus 100 according to a first preferred embodiment of the present invention will be described, which is accomplished by the above-described basic idea.

Figure 1:
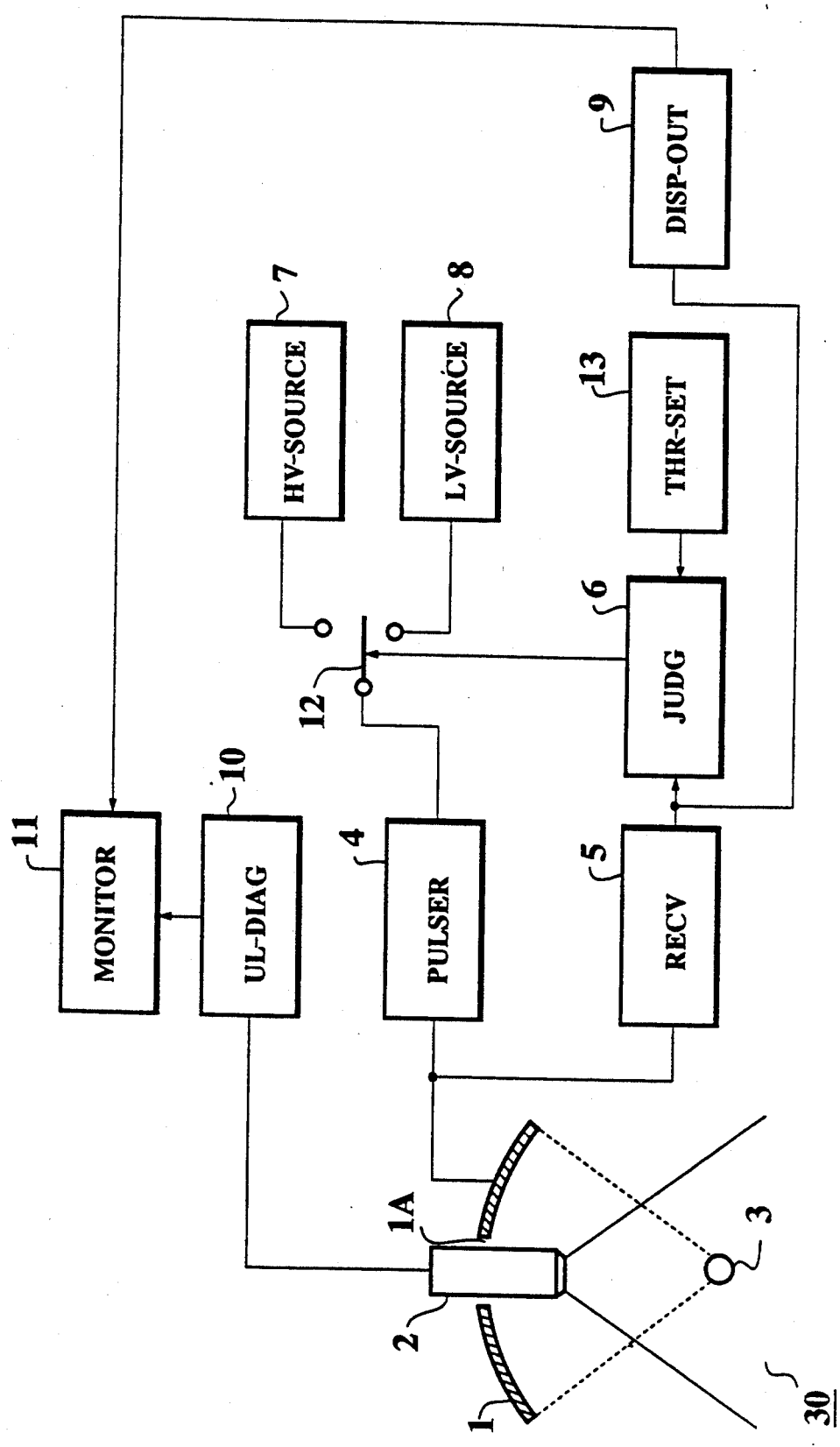
FIG. 1 is a schematic block diagram of the conventional calculus disintegrating apparatus.

As apparent from FIGS. 1 and 2, since the most circuit arrangement of the first calculus disintegrating apparatus 100 is similar to that of the conventional calculus disintegrating apparatus, only different circuits will now be described in the following description.

In the circuit arrangement of the first calculus disintegrating apparatus 100, a maximum/minimum value detecting circuit 20, an automatic threshold value setting circuit 21, a setting instruction switch 22 and a start switch 23 are newly employed in addition to the above-explained major circuit arrangement.

Figure 3:
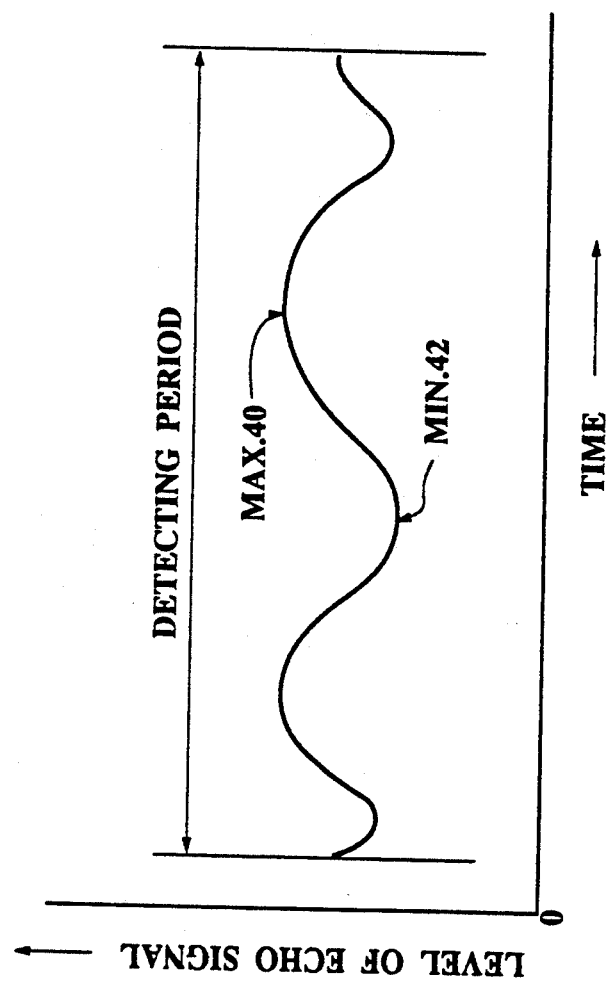
FIG. 3 is a graphical representation between strengths of reflection signals and time with respect to the first calculus disintegrating apparatus 100 shown in FIG. 2.

The function of the maximum/minimum value detecting circuit 20 is to detect both a maximum value 40 and a minimum value 42 (depicted in FIG. 3) by continuously monitoring signal levels of reflection (echo) signals derived from the piezoelectric element 1 via the receiver 5 for a predetermined time period. For instance, as shown in FIG. 3, the detecting period for the echo signals is selected to be 10 seconds which correspond to several respiration times of a human body, and both the maximum signal level 40 and the minimum signal level 42 of the monitored echo signals are detected. As is known, signal levels (strengths) of echo signals reflected from an interior of a biological body 30 are varied in accordance with a respiration time period thereof. In particular, when the echo signals are returned from the calculus 3, a variation width between the maximum signal level and the minimum signal level becomes considerably larger than that of a soft tissue.

The function of the automatic threshold value setting circuit 21 is to automatically set a threshold value suitable for the biological body 30 under medical examination based upon the maximum value 40 and minimum value 42 detected by the maximum/minimum value detecting circuit 20.

The function of the setting instruction switch 22 is to instruct operation timings of the automatic threshold value setting circuit 21. Also, the function of the start switch 23 is to commence an application of shock waves in such a manner that after the judging circuit 6 has made such a judgement that the screening ultrasonic pulses from the piezoelectric element 1 are just focused onto the calculus 3, the pulser 4 is connected via the power switch 12 to the high-voltage power source 7 in order to generate the shock waves from the piezoelectric element 1.

Overall Operation of First Calculus Disintegrating Apparatus

Referring now to FIG. 2, an overall operation of the first calculus disintegrating apparatus 100 will be explained.

First, the switch 12 is so operated that the low-voltage power source 8 is connected to energize the pulser 4. Thus, the screening ultrasonic pulses (i.e., not shock waves) are generated from the piezoelectric element 1 and irradiated to the interior area of the biological body 30 covering the calculus 3.

Thereafter, this interior area is scanned by utilizing the ultrasonic imaging probe 2 so that the ultrasonic tomographic images thereof are monitored on the TV monitor 11 by way of the ultrasonic diagnostic apparatus 10. Thus, an operator can perform positioning (focusing) operation with respect to the calculus 3 while monitoring the tomographic images. The calculus 3 is moved in a horizontal direction (see an arrow of FIG. 2) in response to respiration of the biological body 30, and as a result of the movement of the calculus 3, the signal levels (strengths) of the reflection signals acquired from the piezoelectric element 1 while irradiating the above-described ultrasonic waves to the soft tissue area covering the calculus 3, are changed in accordance with time elapse, more specifically, in response to his respiration, during which the maximum and minimum values are detected and stored.

After the focusing operation for the calculus 3 has been accomplished, the setting instruction switch 22 is turned ON. Thus, the threshold value can be properly and automatically set by the automatic threshold value setting circuit 21 based on the above-detected maximum and minimum values. It should be noted that this threshold value is determined by taking account of the actual conditions (i.e., size, position and shape of the calculus 3) of the individual body 3.

After the threshold value has been calculated or determined, ultrasonic waves are further irradiated onto this interior area whereby echo signals are newly acquired therefrom. Then, the signal strengths of these second echo signals are compared with the above threshold value. If the signal strengths of the second echo signals are higher than this threshold value, the judging circuit 6 can judge that the present ultrasonic waves are just focused onto the calculus 3, so that the switching state of the power switch 12 is changed form the low-voltage power source 8 to the high-voltage power source 7. As a result, the shock waves are generated from the piezoelectric element 1 and can be correctly focused onto the calculus 3, whereby this calculus 3 can be disintegrated.

After this first disintegration operation, ultrasonic waves are again irradiated from the piezoelectric element 1 to the interior area of the biological body 30. Then, signal levels of reflection signals are again compared with the above-described threshold value in order judge whether or not a further (second) application of shock waves can be executed.

Figure 4:
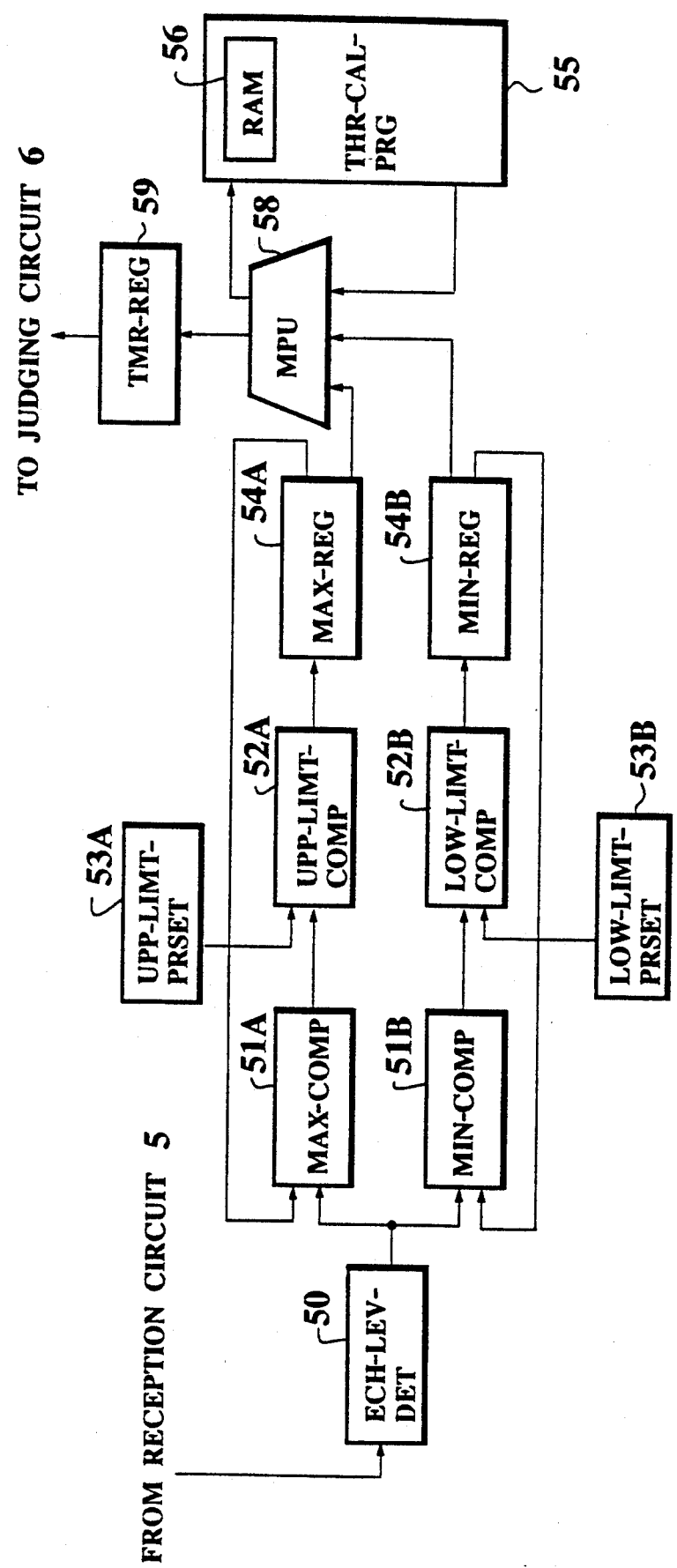
FIG. 4 is a schematic block diagram of an internal circuit arrangement constituting the major circuit of the first calculus disintegrating apparatus 100; and, FIGS. 5A-5D show a timing chart of various signals appearing in the internal circuit arrangement shown in FIG. 4.

Internal Circuit of Main Featured Circuit of First Calculus Disintegrating Apparatus FIG. 4 represents an internal circuit of the maximum/minimum value setting circuit 20 and the automatic threshold value setting circuit 21, which constitute a main featured circuit arrangement of the first calculus disintegrating apparatus 100.

In FIG. 4, the reflection signals are supplied from the receiver 5 shown in FIG. 2 into an echo level detecting circuit 50 so as to detect the echo signal levels thereof. The detected echo signal levels are supplied to both a maximum value comparing circuit 51A and a minimum value comparing circuit 51B, and then the detected echo signal levels are compared with the last maximum value and the last minimum value in the corresponding comparing circuits 51A and 51B, so that the maximum and minimum echo signal levels (see FIG. 3) are finally detected within a predetermined screening time period, for example, 10 seconds or several respiration times of a human body.

Subsequently, the final maximum echo signal level derived from the maximum value comparing circuit 51A is furnished to an upper limit comparing circuit 52A into which an upper limit value has been also supplied from an upper limit preset circuit 53A. It should be noted that this upper limit value has been previously preset in the manufacturing stage of this calculus disintegrating apparatus 100 by measuring such an echo signal level reflected from a phantom, e.g., a metal plate. Since this upper limit value of the echo signal is extremely higher than an echo signal level of a calculus, this may prevent erroneous irradiations of shock waves to any portion (bone) of a biological body other than a calculus. When the upper limit comparing circuit 52A performs such a comparison that the final maximum echo signal level does not exceed this upper limit value, this maximum echo signal level corresponds to the desirable maximum (echo) signal level 40 (see FIG. 3), which will be then stored in a maximum value register 54A.

On the other hand, the final minimum echo signal level derived from the minimum value comparing circuit 51B is furnished to a lower limit comparing circuit 52B into which a lower limit value has been also supplied from a lower limit preset circuit 53B. It should also be noted that this lower limit value has been previously preset in the manufacturing stage by measuring such an echo signal level reflected from a soft tissue around a reference calculus. Since this lower limit value is rather lower than the normal minimum echo signal level, this may also prevent the above-explained erroneous irradiations of shock waves to any portion (soft tissue) of a human body. If the comparison result of the lower limit comparing circuit 52B is made such that the final minimum echo signal level is not lower than this lower limit value, this final minimum echo signal level corresponds to the desirable minimum (echo) signal level 42 (see FIG. 3), which will be then stored in a minimum value register 54B.

In FIG. 4, a memory 55 is employed which previously stores therein a threshold value calculating program and includes a random access memory 56. After reading out the threshold value calculating program from the memory 55, a main processing unit 58 executes the threshold value calculation based upon the maximum signal level stored in the register 54A and also the minimum signal level stored in the register 54B.

In this first preferred embodiment, the threshold value "$T_h$" is calculated by the following equation (1):

$$T_h = \frac{(Max.40 - Min.42) \times A}{2} + Min.42, \quad (1)$$

where symbol "A" indicates a constant.

For instance, if the value of this constant is selected to be 1, then the threshold value "$T_h$" is equal to a half level (value) between the maximum signal level 40 and the minimum signal level 42. It should be noted that the value of this constant "A" is preset and may be varied by an operator, if required.

As a consequence, the calculated threshold value is temporarily stored in a threshold value register 59.

Referring now to a timing chart shown in FIGS. 5A-5D, a sequence of the entire calculus disintegrating operation by the first calculus disintegrating apparatus 100 will now be summarized.

It should be understood that both the maximum and minimum echo signal levels have been detected, and the threshold value has been calculated in accordance with the equation (1), and then stored in the threshold value register 59 as a first threshold value.

In FIG. 5A, when the start switch 23 is turned ON, a starting pulse is produced and supplied to the automatic threshold value setting circuit. As a result, the ultrasonic pulses (see FIG. 5B) are irradiated from the piezoelectric element 1, and thus the echo signals are acquired and processed in the circuit arrangement shown in FIG. 4, whereby the above-described comparisons are performed with reference to the first threshold hold value stored in the threshold value register 59. In this case, assuming now that all of the echo signal levels exceed the first threshold value, a first shock wave as shown in FIG. 5C is focused onto the calculus 3 of the biological body 30.

After application of the first shock wave, as shown in FIG. 5D, the echo pulses are acquired in order to recheck whether or not the above-described first threshold value is still effective for the calculus disintegration by a second shock wave. In this preferred embodiment, since the first threshold value is still effective, the second shock wave is irradiated to the calculus 3. That is, precisely speaking, the signal value of the echo pulse (i.e., a judging echo pulse 60) acquired just before the irradiation timing of the second shock wave is compare with the first threshold value, so that a judgment can be done whether or not a further shock wave irradiation is allowed.

MODIFICATIONS

As apparent from the foregoing description, the present invention is not limited to the above-described preferred embodiment, but may be modified, changed or substituted by other preferred embodiment.

For instance, as a second preferred embodiment, the threshold value "$T_h$" may be determined by the following different formula (2):

$$T_h = \text{Min. } 42 \times A < \text{Max. } 40 \quad (2)$$

Moreover, in the circuit arrangement of FIG. 4, the upper limit comparing circuit 52A, the upper limit preset circuit 53A, the lower limit comparing circuit 52B and the lower limit preset circuit 53B may be omitted. In this example, the threshold value must be determined within a range between the maximum echo signal level (Max. 40 of FIG. 3) and the minimum echo signal (Min. 42 of FIG. 3).

Also, instead of the pulser 4 selectively connected to the high-voltage power source 7 and the low-voltage power source 8 shown in FIG. 2, two different pulsers may be employed. One pulser is connected to the high-voltage power source, whereas the other pulser is connected to the low-voltage power source.

As previously described in detail, according to the present invention, there are particular advantages that since the ultrasonic pulses having low signal levels have been irradiated to the interior region of the patient containing the calculi and the echo signals reflected from the calculi are monitored for a predetermined time period so as to detect the maximum and minimum signal levels, the threshold value suitable for the actual conditions of the individual human body can be automatically determined based on the maximum and minimum signal levels. In other words, this threshold value definitely reflects the individual different conditions of the patient, e.g., the sizes, shapes and positions of the calculi or concretions. Accordingly, such a cumbersome conventional setting operation of the threshold value can be avoided which is conventionally every time the patients are diagnosed. Furthermore, since the shock waves are surely focused onto the concretions under control of the suitably set threshold values, there is no risk to mistakenly give damage to the normal tissue of the body.

What is claimed is:

1. A method for disintegrating a calculus positioned within a biological body under medical examination, said method comprising the steps of:
   irradiating ultrasonic pulses to an interior region of said biological body which contains at least said calculus;
   receiving echo pulses reflected from said interior region of said biological body to produce a first plurality of reflection signals;
   detecting echo signal levels from a portion of said first plurality of reflection signals which is received during a predetermined time period;
   determining both a maximum signal level and a minimum signal level of said echo signal levels;
   setting a first threshold value based on both of said maximum signal level and said minimum signal level; and,
   focusing a shock wave onto said calculus contained in said interior region of said biological body only while signal levels of reflection signals received after setting said first threshold value exceed said first threshold value.

2. A calculus disintegrating method as recited in claim 1, wherein said first threshold value is set within a range between said maximum signal level and said minimum signal level.

3. A calculus disintegrating method as recited in claim 1, further comprising the step of:
   comparing said minimum signal level with a preset lower limit value, whereby only when said minimum signal level exceeds said lower limit value, said minimum signal level is available for setting said first threshold value.

4. A calculus disintegrating method as recited in claim 1, further comprising the step of:
   comparing said maximum signal level with a preset upper limit value, whereby only when said maximum signal level is lower than said preset upper limit value, said maximum signal level is available for setting the first threshold value.

5. A calculus disintegrating method as recited in claim 1, further comprising the steps of:
   secondly irradiating ultrasonic pulses to said calculus, thereby to receive a second plurality of reflection signals; and,
   updating said first threshold value by a second threshold value when at least one signal level of said second plurality of reflection signals received just before irradiation of a subsequent shock wave is lower than said first threshold value.

6. A calculus disintegrating method as recited in claim 1, wherein said predetermined time period is selected to be approximately 10 seconds.

7. A calculus disintegrating apparatus comprising:
   means for irradiating ultrasonic pulses to an interior region of a biological body which contains at least a calculus;
   means for receiving echo pulses reflected from said interior region of said biological body to produce a plurality of reflection signals;
   means for detecting signal levels of a portion of said plurality of reflection signals which is received during a predetermined time period;
   means for determining both a maximum and minimum signal level of said signal levels;
   means for setting a first threshold value based upon both of said maximum signal level and said minimum signal level;
   means for judging whether or not signal levels of reflection signals received after said first threshold value is set exceed said first threshold value to produce a judging signal; and,
   means for focusing a shock wave onto the calculus contained in said interior region of said biological body in response to said judging signal.

8. A calculus disintegrating apparatus as recited in claim 7, wherein said determining means includes:
   maximum value comparing circuit means for comparing said signal levels with a preset maximum value; and,
   minimum value comparing circuit means for comparing said signal levels with a preset minimum value.

9. A calculus disintegrating apparatus as recited in claim 7, further comprising:
   lower limit preset circuit means for presetting a lower limit value; and,
   lower limit comparing circuit means for comparing said minimum signal level with said lower limit value, whereby only when said minimum signal level exceeds said lower limit value, said minimum signal level is available for setting said first threshold value.

10. A calculus disintegrating apparatus as recited in claim 7, further comprising:
    upper limit preset circuit means for presetting an upper limit value; and,
    upper limit comparing circuit means for comparing said maximum signal level with said upper limit value, whereby only when said maximum signal level is lower than said preset upper limit value, said maximum signal level is available for setting said first threshold value.

11. A calculus disintegrating apparatus as recited in claim 7, wherein said setting means updates said first threshold value by a second threshold value when at least one signal level of a reflection signal received just before irradiation of a subsequent shock wave is lower than said first threshold value.

12. A calculus disintegrating apparatus as recited in claim 7, wherein said setting means sets said first threshold value within a range between said maximum signal level and said minimum signal level.

13. A calculus disintegrating apparatus as recited in claim 7, wherein said receiving means continuously receives the echo pulses for approximately 10 seconds.

* * * * *